(12) United States Patent
Borgmeier et al.

(10) Patent No.: US 11,446,416 B2
(45) Date of Patent: *Sep. 20, 2022

(54) VACUUM ASSISTED IRRIGATION PUMP

(71) Applicant: Megadyne Medical Products, Inc., Draper, UT (US)

(72) Inventors: Paul R. Borgmeier, Salt Lake City, UT (US); Darcy W. Greep, Herriman, UT (US); Shawn K. Horner, Woods Cross, UT (US); Chad S. Frampton, American Fork, UT (US)

(73) Assignee: Megadyne Medical Products, Inc., Draper, UT (US)

(*) Notice: Subject to any disclaimer, the term of this patent is extended or adjusted under 35 U.S.C. 154(b) by 125 days.

This patent is subject to a terminal disclaimer.

(21) Appl. No.: 16/682,533

(22) Filed: Nov. 13, 2019

(65) Prior Publication Data

US 2020/0078498 A1    Mar. 12, 2020

Related U.S. Application Data

(63) Continuation of application No. 15/632,305, filed on Jun. 24, 2017, now Pat. No. 10,478,533.

(51) Int. Cl.
*A61M 1/00* (2006.01)
*A61M 5/145* (2006.01)
(Continued)

(52) U.S. Cl.
CPC ............ *A61M 1/0058* (2013.01); *A61M 1/80* (2021.05); *A61M 1/802* (2021.05);
(Continued)

(58) Field of Classification Search
CPC .............. A61M 1/0074; A61M 3/0233; A61M 2005/14553; A61M 5/1483; A61M 5/1486
See application file for complete search history.

(56) References Cited

U.S. PATENT DOCUMENTS

| 4,058,123 A | 11/1977 | May |
| 4,112,947 A | 9/1978 | Nehring |

(Continued)

FOREIGN PATENT DOCUMENTS

| CN | 102427780 | 4/2012 |
| CN | 104640581 | 5/2015 |
| EP | 2432433 A1 | 3/2012 |

OTHER PUBLICATIONS

Non-Final Office Action for U.S. Appl. No. 15/632,305 dated Apr. 8, 2019.

(Continued)

*Primary Examiner* — Emily L Schmidt
(74) *Attorney, Agent, or Firm* — Workman Nydegger

(57) ABSTRACT

Embodiments of the present invention relate to the field of pressurized fluid delivery devices for use in medical procedures. In particular, a fluid delivery pump comprises at least one compressive member configured to apply a force to a fluid reservoir. The at least one compressive member is associated with a flexible envelope, such that the flexible envelope may move the compressive member. The flexible envelope may be substantially air-tight so that it may be pressurized. When a negative pressure is created inside the flexible envelope, the flexible envelope may change volume, applying a force to the at least one compressive member. The at least one compressive member may then apply a force to the fluid reservoir and the fluid is forced out of the reservoir.

20 Claims, 11 Drawing Sheets

(51) Int. Cl.
*A61M 3/02* (2006.01)
*A61M 5/148* (2006.01)

(52) U.S. Cl.
CPC .......... *A61M 3/0233* (2013.01); *A61M 5/145* (2013.01); *A61M 5/148* (2013.01); *A61M 5/14593* (2013.01)

(56) References Cited

U.S. PATENT DOCUMENTS

| | | | |
|---|---|---|---|
| 5,013,303 A * | 5/1991 | Tamari | A61M 5/1483 |
| | | | 128/DIG. 12 |
| 5,248,300 A | 9/1993 | Bryant et al. | |
| 6,099,492 A | 8/2000 | Le Boeuf | |
| 6,358,239 B1 | 3/2002 | Rake et al. | |
| 7,806,865 B1 | 10/2010 | Wilson | |
| 8,136,779 B2 | 3/2012 | Wilson et al. | |
| 10,478,533 B2 | 11/2019 | Borgmeier et al. | |
| 2007/0250008 A1 | 10/2007 | Gelblum | |
| 2011/0019630 A1 | 1/2011 | Harris | |
| 2011/0196304 A1 | 8/2011 | Kramer et al. | |
| 2014/0100518 A1 | 4/2014 | Baxter et al. | |
| 2014/0114237 A1 | 4/2014 | Gordon | |
| 2014/0243738 A1 | 8/2014 | Kramer et al. | |
| 2016/0015599 A1 * | 1/2016 | Gentile | B67D 7/0261 |
| | | | 222/1 |

OTHER PUBLICATIONS

Restriction Requirement for U.S. Appl. No. 15/632,305 dated Dec. 28, 2018.

International Search Report for Patent Cooperation Treaty application No. PCT/IB2018/053399 dated Oct. 18, 2018.

* cited by examiner

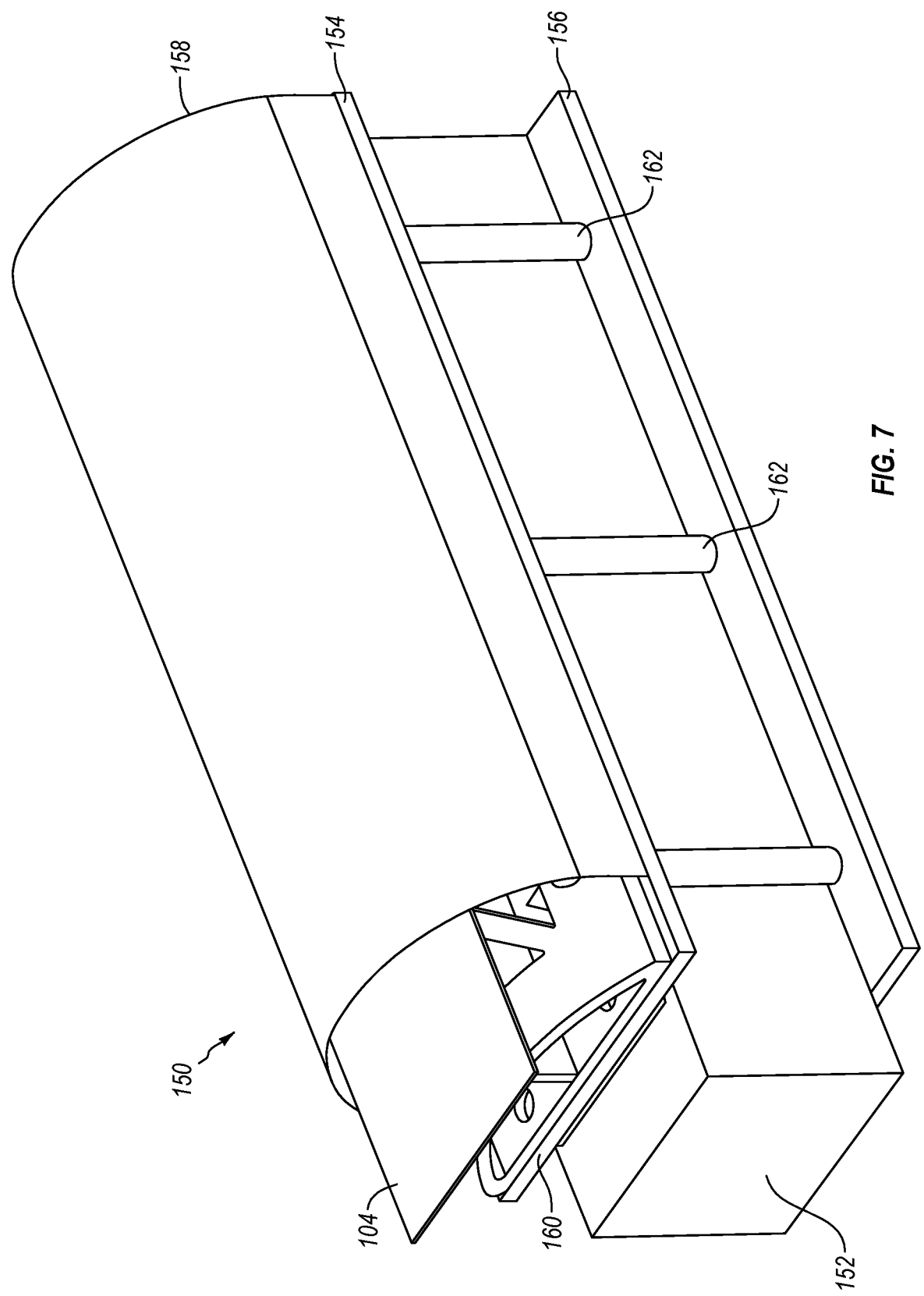

VACUUM ASSISTED IRRIGATION PUMP

CROSS-REFERENCE TO RELATED APPLICATIONS

This application is a continuation of U.S. patent application Ser. No. 15/632,305, filed Jun. 24, 2017, entitled "VACUUM ASSISTED IRRIGATION PUMP," the disclosure of which is incorporated herein by this reference.

BACKGROUND

1. The Field of the Invention

Embodiments of the present invention generally relate to the medical device field. More specifically, embodiments of the present invention relate to the field of systems, methods, and devices for irrigating open wounds or incisions in a hospital or medical office environment.

2. The Relevant Technology

Irrigation systems are typically used in medical settings to provide either a continuous or pulsed pressurized stream of sterile solution to an open wound or incision. An irrigation system provides a way of clearing away debris from wounds, such as dirt from a laceration, or clearing away blood from incisions to provide a practitioner a clearer view of a particular area without introducing surgical tools or exposing technicians to the patient's blood themselves.

The fluid in irrigation systems is typically pressurized by creating a pressurized environment in the sterile irrigation fluid reservoir. This can be done in several ways. The simplest form is the use of a gravity feed. A technician can suspend a sterile irrigation fluid reservoir at a height above the irrigation area and the irrigation solution will effectively "fall" to the irrigation area. The potential energy imparted by the height differential will partially convert to kinetic energy, allowing the technician to direct an energized flow to the desired irrigation region.

The most common method of providing a gravity feed is suspension of the sterile irrigation fluid reservoir from a mobile pole, commonly known as an IV (Intravenous) stand or IV pole. However, this method is limited by the height differential available in the setting immediately surrounding the patient, such as the availability of IV stands or the height of a ceiling. Furthermore, the rate of delivery of the sterile irrigation fluid is also dependent upon the height of the sterile irrigation fluid reservoir. Thus, the pressure and flow rate may change based on the height differential and the amount of fluid in the reservoir.

Another method of pressurization is the compression of the exterior of the sterile irrigation fluid reservoir by placing the sterile irrigation fluid reservoir in an atmosphere of positive pressure. That method can attain higher possible pressurization than a gravity feed, however it requires a pump local to the chamber in which the sterile irrigation fluid reservoir is housed. Such a system may employ a chamber with a positive pressure atmosphere created by an attached air pump. This method therefore requires the availability of a pump and chamber system as well as moving a heavy, proprietary pump with the chambers.

Yet another method of pressurization is the pressurization of the sterile irrigation solution by an in-line pump. An in-line pump may provide a very stable but adjustable pressure on for the sterile irrigation solution, but all pressure is lost upon deactivation of the pump. Therefore, without an available pump, there is no pressure whatsoever to deliver solution from the sterile irrigation solution reservoir.

Yet another method of pressurization is the compression of the exterior of the sterile irrigation solution reservoir by mechanical compression. For instance, such systems may use a hand pump to inflate an outer cuff around a sterile irrigation solution reservoir, thereby applying a compression force to the sterile irrigation solution reservoir and forcing the irrigation solution out of the reservoir. However, as the solution drains out and the volume of the reservoir decreases, the force from the cuff decreases and the operator must monitor and adjust the application of force via the outer cuff as needed to maintain pressure on the sterile irrigation solution reservoir.

Thus, there are a number of problems with irrigation systems that can be addressed by embodiments of the present invention.

BRIEF SUMMARY OF THE INVENTION

Embodiments according to the present invention relate to the field of irrigating wounds and incisions during medical procedures.

In an embodiment of the present invention, an irrigation pump comprises a flexible envelope configured to contain a fluid reservoir therein. At least one compressive member is disposed in contact with the flexible envelope to provide structure and to apply force to the fluid reservoir to pressurize the fluid therein. A conduit provides fluid communication between an exterior of the flexible envelope and the fluid reservoir disposed inside the flexible envelope.

In another embodiment of the present invention, an irrigation pump comprises a substantially air-tight flexible envelope, a fluid reservoir disposed inside the flexible envelope, and a plurality of at least semi-rigid compressive members. The flexible envelope may have a valve in the surface of the envelope configured such that a user may create a negative pressure within the flexible envelope. The plurality of at least semi-rigid compressive members is configured to apply a compressive force to the fluid reservoir when a negative pressure is created in the flexible envelope. When the fluid reservoir is compressed, the fluid in the fluid reservoir may become pressurized. The irrigation pump may also include a fluid conduit so that the pressurized fluid may exit the fluid reservoir.

In yet another embodiment according to the present invention, an irrigation pump comprises a flexible envelope having a length, width, and height. Inside that flexible envelope are first and second at least semi-rigid compressive members having a length and width substantially equal to the length and width of the flexible envelope. Between the two at least semi-rigid compressive members may be a fluid reservoir that is in fluid communication with a conduit to the exterior of the flexible envelope. The flexible envelope also has a valve in its surface to allow a user to pump air out of the flexible envelope, thereby creating a region of negative pressure inside the envelope and a pressure differential across the envelope's surface. When the user does so, the at least semi-rigid compressive members apply a force to the fluid reservoir and the pressurized fluid therein is forced through the conduit.

In a yet further embodiment of the present invention, an irrigation pump comprises a plurality of compressive members. A fluid reservoir may be disposed between the compressive members and the compressive members may be connected to a flexible envelope. The flexible envelope may be connected to the compressive members such that when the flexible envelope changes volume, the flexible envelope moves at least one of the compressive members. The flexible envelope may be in fluid communication with a valve that allows the creation of a negative pressure within the flexible envelope. The compressive members may be inside or outside of the flexible envelope, and at least one of the compressive members may be connected to the flexible envelope by a mechanical link.

In yet another embodiment according to the present invention, an irrigation pump is part of a system. The system may also include a vacuum pump and an irrigation wand. The vacuum pump is connected to a valve in the irrigation pump's surface and helps create the negative pressure within the envelope. The irrigation wand is connected to the conduit through an irrigation tube and allows a user to direct the pressurized fluid exiting the irrigation pump and traveling through the irrigation tube.

Such embodiments require no additional power sources and have few moving parts. By leveraging atmospheric pressure and the vacuum systems available in most hospitals, a low-cost portable irrigation pump may be provided. In addition, an irrigation pump according to the present invention may require limited or negligible draw on a hospital vacuum system and may be reusable. Taken together, such an irrigation pump may limit waste and energy consumption, as well as provide a versatile irrigation pump that is durable and has low operation costs.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 7 depicts a perspective view of another embodiment of a vacuum-assisted irrigation pump.

DETAILED DESCRIPTION OF THE PREFERRED EMBODIMENTS

Embodiments of the present invention generally related to the medical device field. More specifically, embodiments of the present invention relate to systems, methods, and devices for delivering a pressurized fluid during medical procedures in a hospital or medical office environment.

For example, irrigation pumps according to the present invention allow for a portable source of pressurized irrigation fluid while utilizing the readily available central vacuum system in most modern hospitals or other vacuum pump. The irrigation pump pressurizes a fluid reservoir within the pump to force the irrigation fluid out in a directable stream. However, unlike other irrigation pumps, it does not create a chamber of positive pressure to pressurize the fluid. Irrigation pumps according to the present invention rely upon the natural atmospheric pressure to create a compressive force to pressurize a fluid reservoir inside the pump. The central vacuum system or other vacuum pump may be used to create a region of negative pressure (air pressure below the atmospheric pressure) within a substantially air-tight flexible envelope to create a compressive force on the exterior surface of the pump. The compressive force is therefore amplified relative to the smaller exterior surface of the fluid reservoir, and this difference in relative surface area leads to a pressurization of the fluid therein.

In many cases, embodiments of the invention may be used in a hospital setting. Many modern hospitals have a central vacuum system that runs throughout the building and into each room. There is an outlet in the wall that will provide negative pressure according to guidelines established by the National Fire Protection Associations Standard. Under NFPA 99-1996 § 4-3.4.2.1, the vacuum provides 85 L/min flow at one inlet and the pressure should not drop below 305 mmHg at an adjacent outlet. Therefore, the vacuum, by regulation, may provide a relatively stable source of 305 millimeters of mercury (mmHg) negative pressure without going below that value. 305 mmHg of pressure differential below standard air pressure creates a net 5.90 absolute pounds per square inch (psia) acting upon the pressurized body. The NFPA regulation sets a standard for hospital vacuum systems, however, a valve disposed at the inlet may further regulate the flow and thereby allow an operator to further adjust the pressure supplied by the system.

Alternatively, the vacuum pump may be a local system that is attached to the irrigation pump. The flow rate and pressure provided by a local pump can vary and it will be understood that a local pump may provide the aforementioned flow rate and pressure. Therefore, the aforementioned rate and pressure will be used for exemplary purposes and without intent to limit the present invention.

Figure 1:
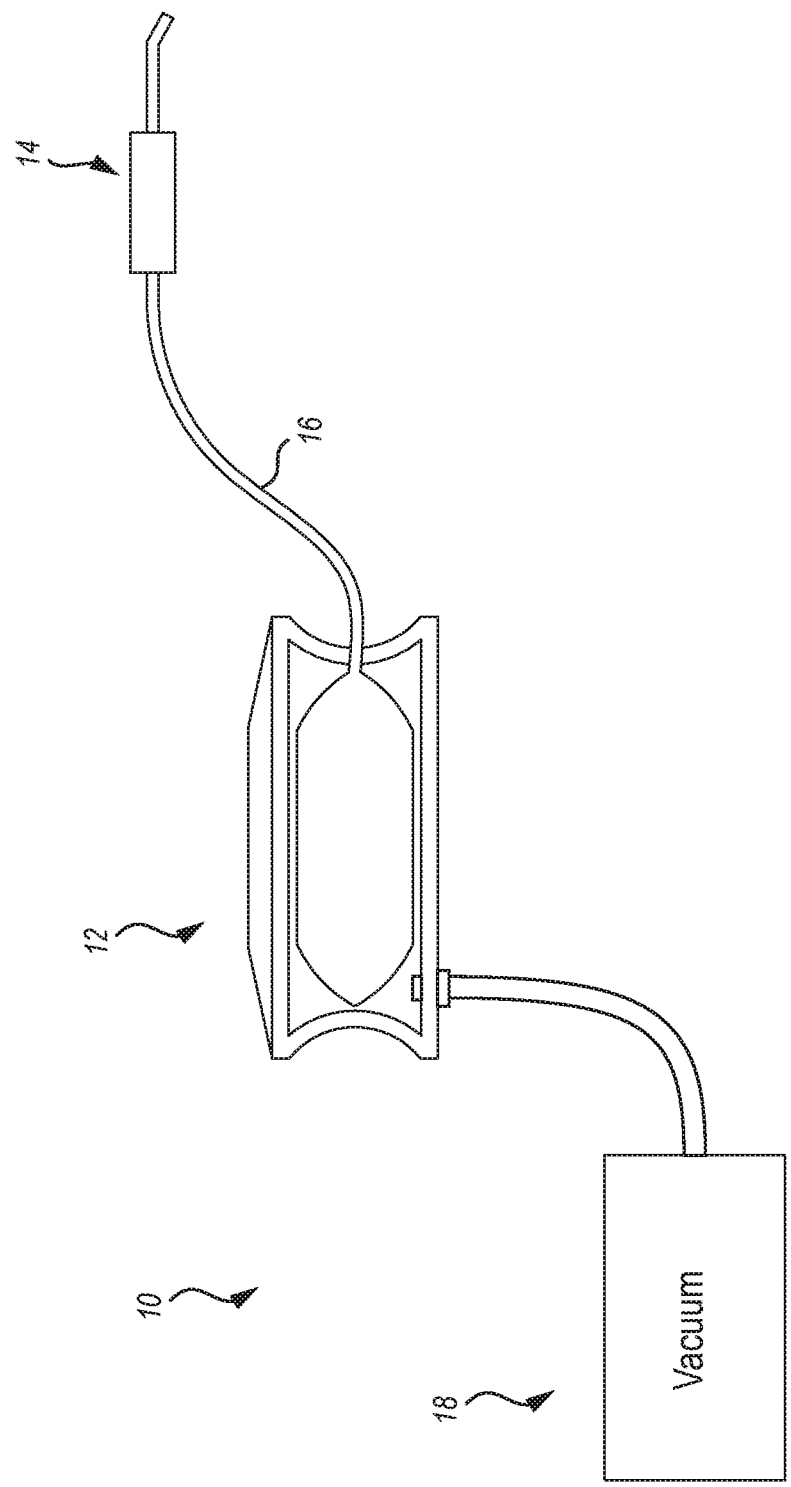
FIG. 1 illustrates a system according to an example embodiment of the present invention.

FIG. 1 illustrates an irrigation system 10 according to an embodiment of the present invention. Irrigation system 10 includes an irrigation pump 12 that may deliver a sterile irrigation solution to irrigation wand 14 through an irrigation tube 16 with energy provided by vacuum 18. The irrigation pump 12 may use the force created by a pressure differential between the exterior atmospheric pressure and a partial vacuum (this difference commonly referred to as "negative pressure") disposed within the irrigation pump 12. The negative pressure may be provided by fluid communication of the irrigation pump 12 with a vacuum pump 18. The net force on the irrigation pump may be used to pressurize a fluid reservoir and deliver a pressurized stream of fluid to the irrigation wand 14.

Figure 2:
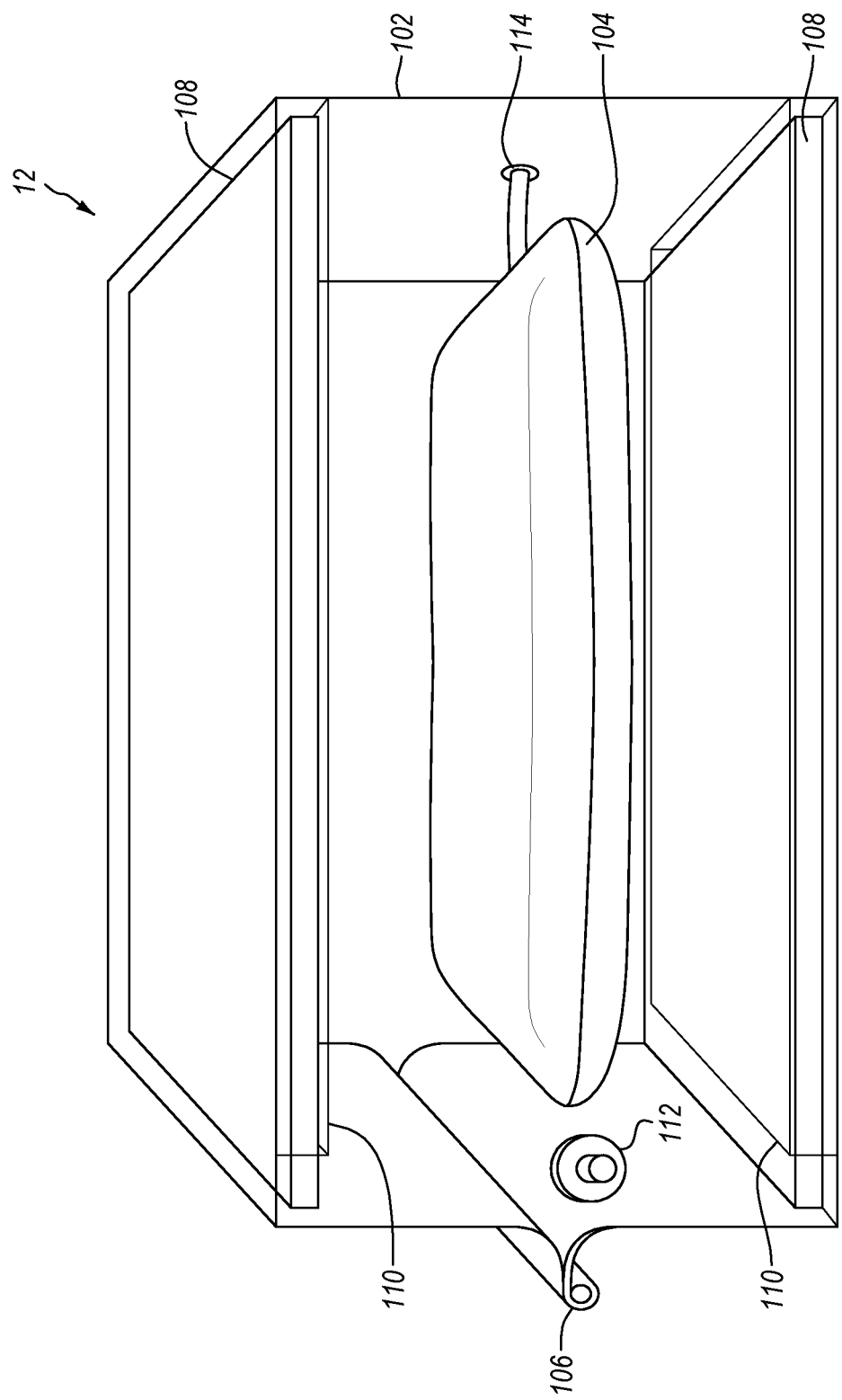
FIG. 2 illustrates a side view of a vacuum-assisted irrigation pump shown in FIG. 1.
Figure 3:
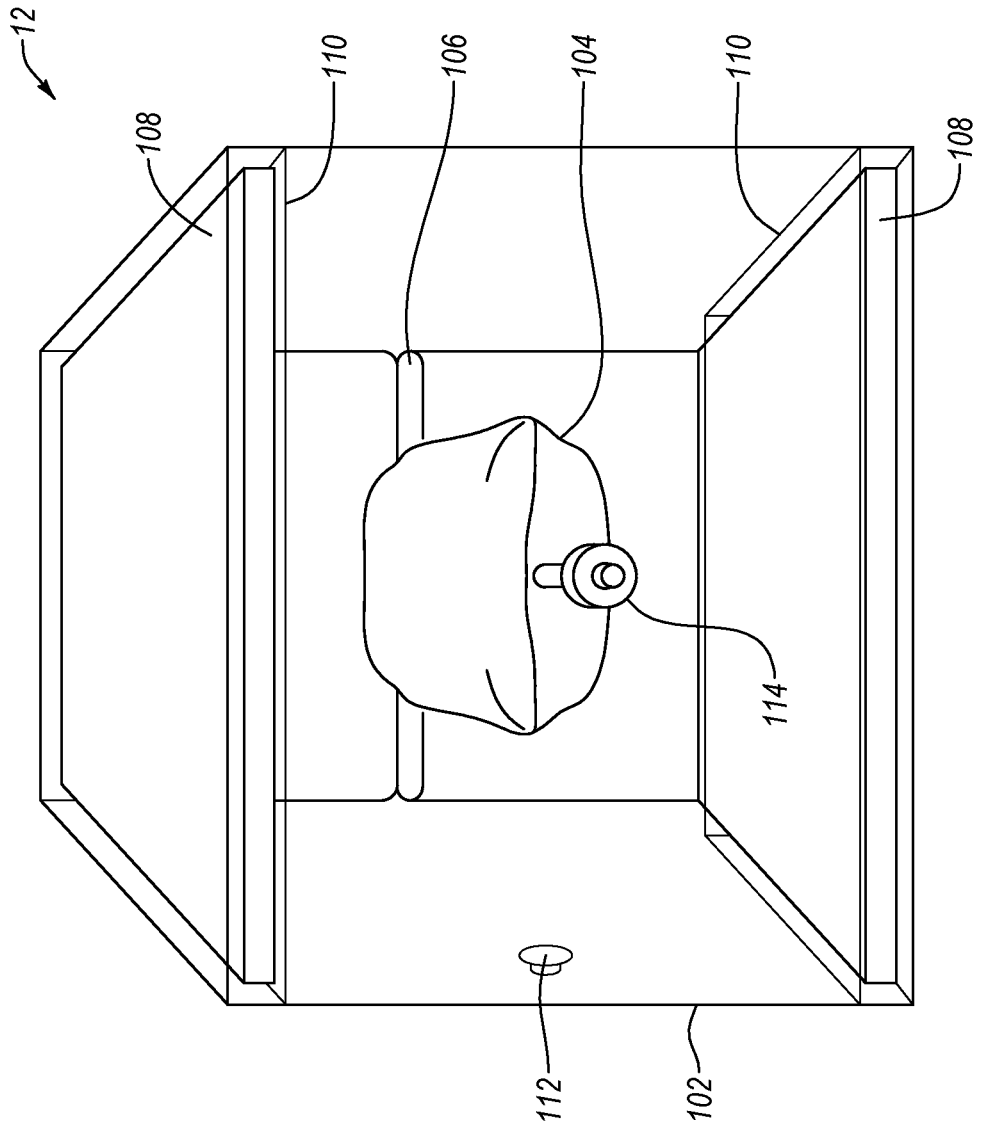
FIG. 3 illustrates an end view of the vacuum-assisted irrigation pump shown in FIG. 2.

FIGS. 2 and 3 depict the irrigation pump 12 in side and end views, respectively. In an embodiment, the irrigation pump 12 has a flexible envelope 102 with six surfaces such as a cube, rectangular prism, or trapezoidal prism. In another embodiment, the flexible envelope 102 may be cylindrical. In yet another embodiment, the flexible envelope 102 may have two surfaces of similar dimensions such that the two may be joined at a single seam running the perimeter of the surfaces. In yet another embodiment, the flexible envelope 102 may be constructed of an elastic material. The elastic material may allow for types of construction that will elastically deform to match the dimensions or shape necessary to operate with other components. The flexible envelope 102 may also be constructed in any fashion such that the envelope may collapse in at least one dimension such that an enclosed fluid reservoir 104 may be compressed.

The flexible envelope 102 may define a flexible chamber configured to house a fluid reservoir 104. In an embodiment, the fluid reservoir 104 may be a commercially available irrigation fluid reservoir, such as a 1 liter saline solution reservoir, installed by a user. In another embodiment, the reservoir may be integral to the construction and may not be replaceable by a user. In an embodiment, at least a portion of the flexible envelope 102 may be transparent to allow the visual inspection of the contents of the flexible envelope 102. A transparent flexible envelope 102 may also assist in insertion, removal, or adjustment of components inside the flexible envelope 102.

Still referring to FIGS. 2 and 3, the flexible envelope 102 may have an opening 106 to permit the fluid reservoir 104 to be inserted into the interior of the flexible envelope 102. In an embodiment, the opening 106 may incorporate a roll-closure with clips such as that on a SEALLINE ECO-SEE Dry Bag. In another embodiment, the opening 106 may incorporate a zipper, clasp locker, ZIP-LOC-style closure, one or more gel surfaces, adhesive, cohesive tape, or any other type of closure to selectively seal the bag in a substantially air-tight fashion. The opening 106 may also be large enough to permit the insertion, removal or adjustment of compressive members 108.

Compressive members 108 may be made of wood, metal, plastic, ceramic, or any other material that allows for a distribution of compressive forces across the surface of the compressive member 108. In an embodiment, the compressive members 108 may be disposed within the flexible envelope 102. In another embodiment, the compressive members may be connected to an outer surface of the flexible envelope 102. In still another embodiment, the compressive members 108 may be integrated into the flexible envelope 102. In an embodiment, the compressive members 108 have a length and width that substantially match the analogous dimensions of the flexible envelope 102. The compressive members 108, in another embodiment, may have dimensions that vary from those of the flexible envelope 102. In particular, the dimension of the compressive members 108 may vary from the dimensions of the flexible envelope 102 when the flexible envelope 102 is of the two-surface type described above. This two-surface type of flexible envelope 102 may have a length and width greater than that of the compressive members 108 to allow the edges of the flexible envelope 102 to deform when the compressive members 108 are disposed surrounding a fluid reservoir 104.

The compressive members 108 each may be disposed within a sleeve 110, respectively. The sleeves 110 may be closed or may be open at one or more locations to allow the removal, replacement or adjustment of compressive members 108. Compressive members 108 of different dimensions may provide compressive forces of different magnitudes. Alternatively, the compressive members 108 may be secured to a position within the flexible envelope 102 by adhesive, hook-and-loop, or other fasteners to ensure the compressive members 108 are retained in a particular location relative to one another, the flexible envelope 102 and/or the fluid reservoir 104. In another embodiment, the compressive members 108 may be movably affixed to one another, such as with a hinge, to ensure the compressive members 108 are retained in a particular location relative to one another and the fluid reservoir 104. In yet another embodiment, compressive members 108 may be at least semi-rigid to transfer force to the fluid reservoir 104 while offering some compliance to mitigate sudden changes in pressure.

The irrigation pump 12 may also include a vacuum connection 112 to provide fluid communication between a vacuum pump 18 or other fluid pump (visible in FIG. 1) and the interior of the flexible envelope 102, thereby allowing for the evacuation of the interior of the flexible envelope 102. In an embodiment, the vacuum connection 112 may be a one-way valve to allow for manual compression of the flexible envelope 102 without air or another fluid reentering the flexible envelope 102 after release of the manual compression force. In another embodiment, the vacuum connection 112, may only allow for the passage of air or another fluid upon the connection of a vacuum pump 18 to the vacuum connection 112, thereby ensuring the maintenance of a specific quantity of air inside the flexible envelope 102 once attained.

The irrigation pump 12 may comprise a reservoir connection 114. The reservoir connection 114 may allow fluid from the fluid reservoir 104 to exit the irrigation pump 12 and flow to an irrigation wand 14 (visible in FIG. 1). In an embodiment, the reservoir connection 114 may be a one-way valve to prevent fluid or air from entering the fluid reservoir 104 during operation. In another embodiment, the reservoir connection 114 may be a connection that only allows for the passage of fluid when an irrigation wand 14 (visible in FIG. 1) is connected to the reservoir connection 114 to prevent accidental discharge of fluid from the fluid reservoir 104.

Figure 4:
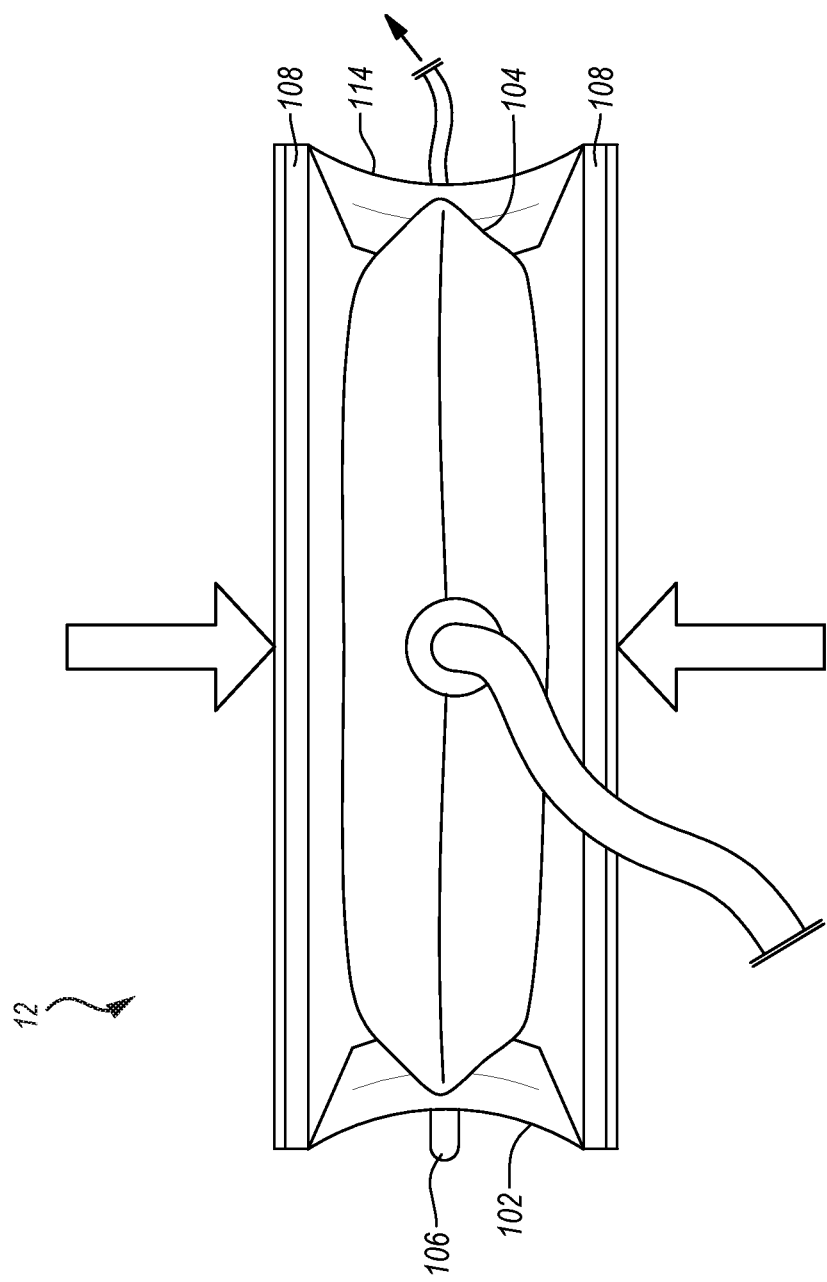
FIG. 4 depicts the evacuation of air from the interior of the vacuum-assisted irrigation pump shown in FIG. 2.

FIG. 4 depicts the evacuation of the flexible envelope 102. Upon evacuation of the flexible envelope 102, atmospheric pressure creates a pressure differential across the flexible envelope 102 due to the negative pressure within the flexible envelope 102. This pressure urges the compressive members 108 towards the center of the irrigation pump 12, and causes a compressive force on the fluid reservoir 104. The compressive force on the fluid reservoir 104 increases pressure within the fluid reservoir 104, causing fluid to exit the fluid reservoir 104 through the reservoir connection 114. This may be due, at least in part, to the larger surface area of the compressive members 108 than the surface area of the fluid reservoir 104.

Figure 5:
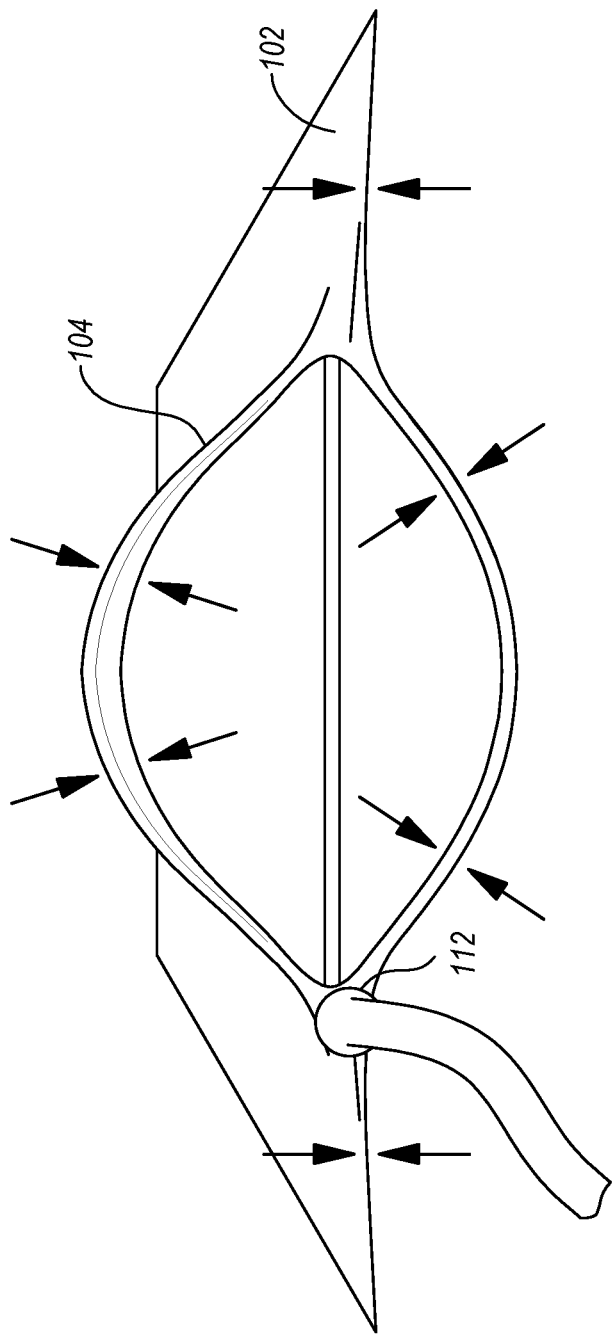
FIG. 5 depicts an inoperable configuration of a device lacking compressive members.

As can be seen in FIG. 5, if the compressive members 108 are removed from the flexible envelope 102 and the flexible envelope 102 is then evacuated, atmospheric pressure will deform the flexible envelope 102, conforming it to the shape of the fluid reservoir 104. Because the fluid in the fluid reservoir 104 is at or near atmospheric pressure, upon evacuation of the flexible envelope 102, the pressure will be about 760 mmHg or 14.696 psia on opposing sides of the flexible envelope 102, as well as inside the fluid reservoir 104, leading to a pressure equilibrium and no net force on any part of the irrigation pump 12 due to atmospheric pressure.

By contrast, if the compressive members 108 are included, as in FIG. 4, the larger surface area of the compressive members 108 compared to the fluid reservoir 104, provides a net compressive force when both the surface area of the compressive members 108 (by way of the flexible envelope) and the fluid reservoir 104 (by way of the reservoir connection) are each subject to the same atmospheric pressure.

Therefore, the effective ratio of the surface area of the compressive members 108 to the surface area of the fluid reservoir 104, may contribute to the amount of force applied to the fluid inside the fluid reservoir 104. In an embodiment, the ratio of the surface area of the compressive members 108 to the surface area of the fluid reservoir 104 is less than about 3:2. In another embodiment, the ratio of the surface area of the compressive members 108 to the surface area of the fluid reservoir 104 is between about 3:2 and about 2:1. In yet another embodiment, the ratio of the surface area of the compressive members 108 to the surface area of the fluid reservoir 104 is greater than about 2:1.

Figure 6A:
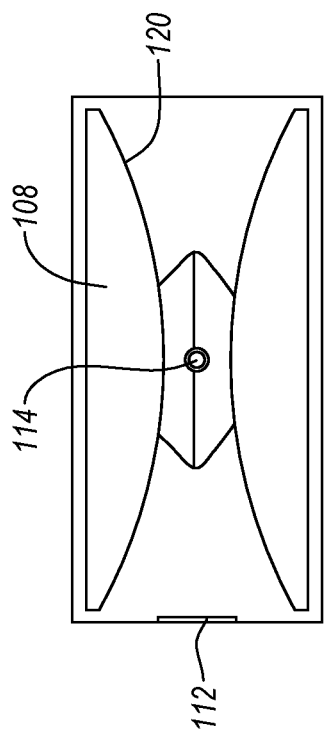
FIGS. 6A-D depict alternative embodiments of the compressive members similar to those in the vacuum-assisted irrigation pump of FIG. 2.

FIGS. 6A-6D depict a selection of example embodiments for the compressive members 108. FIG. 6A illustrates a hinged set of compressive members 108. In an embodiment, the hinge 118 may be disposed opposite the vacuum connection 112. A hinged configuration may enable a more efficient transfer of the force from the pressure differential to compress the fluid reservoir 104. The hinge 118 depicted in FIG. 6A is disposed laterally with respect to the reservoir connection 114, but a configuration in which the hinge 118 is disposed at the opposite end from the reservoir connection 114 is contemplated as well. Such a configuration may be desirable to urge more of the fluid in the fluid reservoir 104 toward the end of the fluid reservoir 104 nearest the reservoir connection 114 during compression.

Figure 6B:
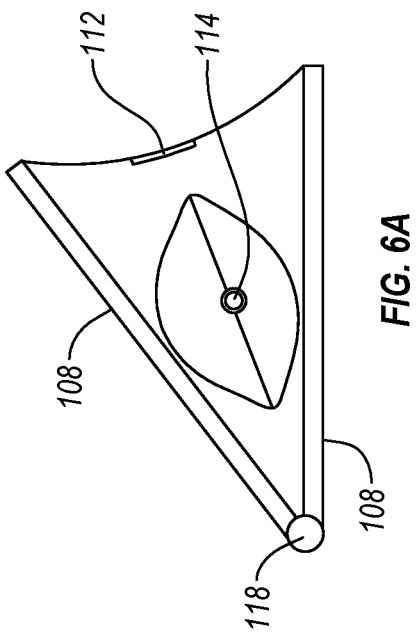

FIG. 6B depicts an embodiment in which the compressive members 108 have a curved interior surface 120. A curved interior surface 120 may further focus the force of the pressure differential upon the fluid reservoir 104 and ensure the fluid reservoir 104 is compressed consistently while the flexible envelope 102 collapses and as fluid exits the fluid reservoir 104 and the volume of both the fluid reservoir 104 and the irrigation pump 12 decreases. While the curvature of the compressive members 108 is depicted laterally with respect to the reservoir connection 114, it should be understood that the curvature may also exist at any orientation in addition or alternative.

Figure 6C:
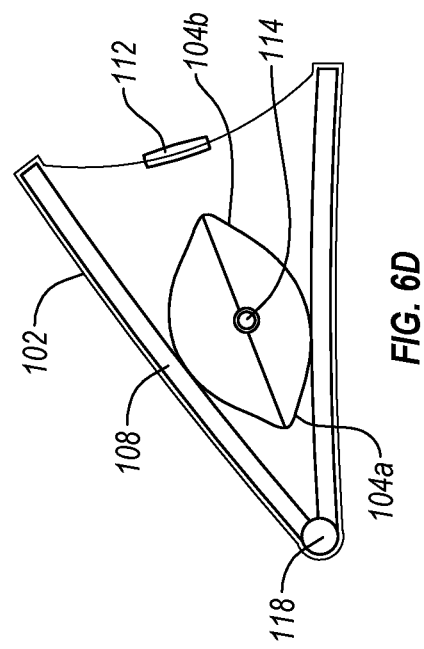

FIG. 6C illustrates an alternative embodiment in which the compressive members 108 comprise a textured or ridged surface 122 to further focus the force of the pressure differential against the fluid reservoir 104. The ridges 122 reduce the effective contact area of the compressive members 108 with the fluid reservoir 104. The force applied to the fluid reservoir is defined as $$F = (A_1 - A_2) \Delta P \quad (1)$$

where $A_1$ is the area over which the external force is applied, $A_2$ is the area over which the internal force is applied, $\Delta P$ is the pressure differential between the interior and the exterior of the envelope, and F is the force applied. The advantage of a reduced effective area is an increased pressure on the fluid reservoir 104 along the ridges 122 because the atmospheric pressure remains the same on the exterior of the flexible envelope and the area difference increases.

The grooves 122 may be aligned in the direction of the reservoir connection 114 such that the length of the fluid reservoir 104 may remain in fluid communication with the reservoir connection 144 and therefore an irrigation wand 14 even when the compressive members 108 compress the fluid reservoir 104 to a point where the compressive members 108 begin to urge opposite surfaces of the fluid reservoir 104 into contact with one another. Again, while the texturing or grooves 122 of the compressive members 108 is depicted longitudinally with respect to the reservoir connection 114, it should be understood that the texturing or grooves 122 may also exist at any orientation in addition or in the alternative.

Figure 6D:
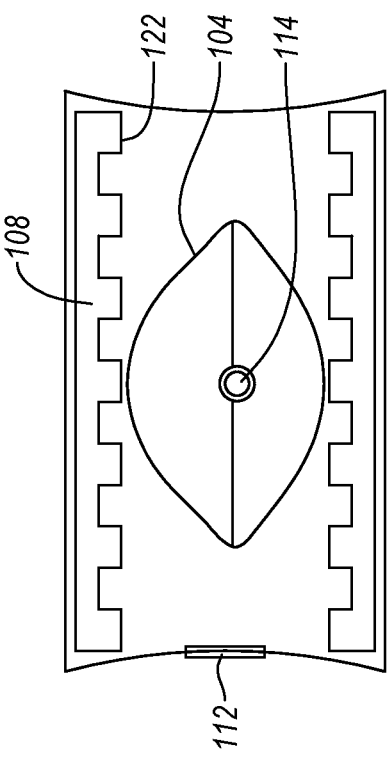
Figure 8:
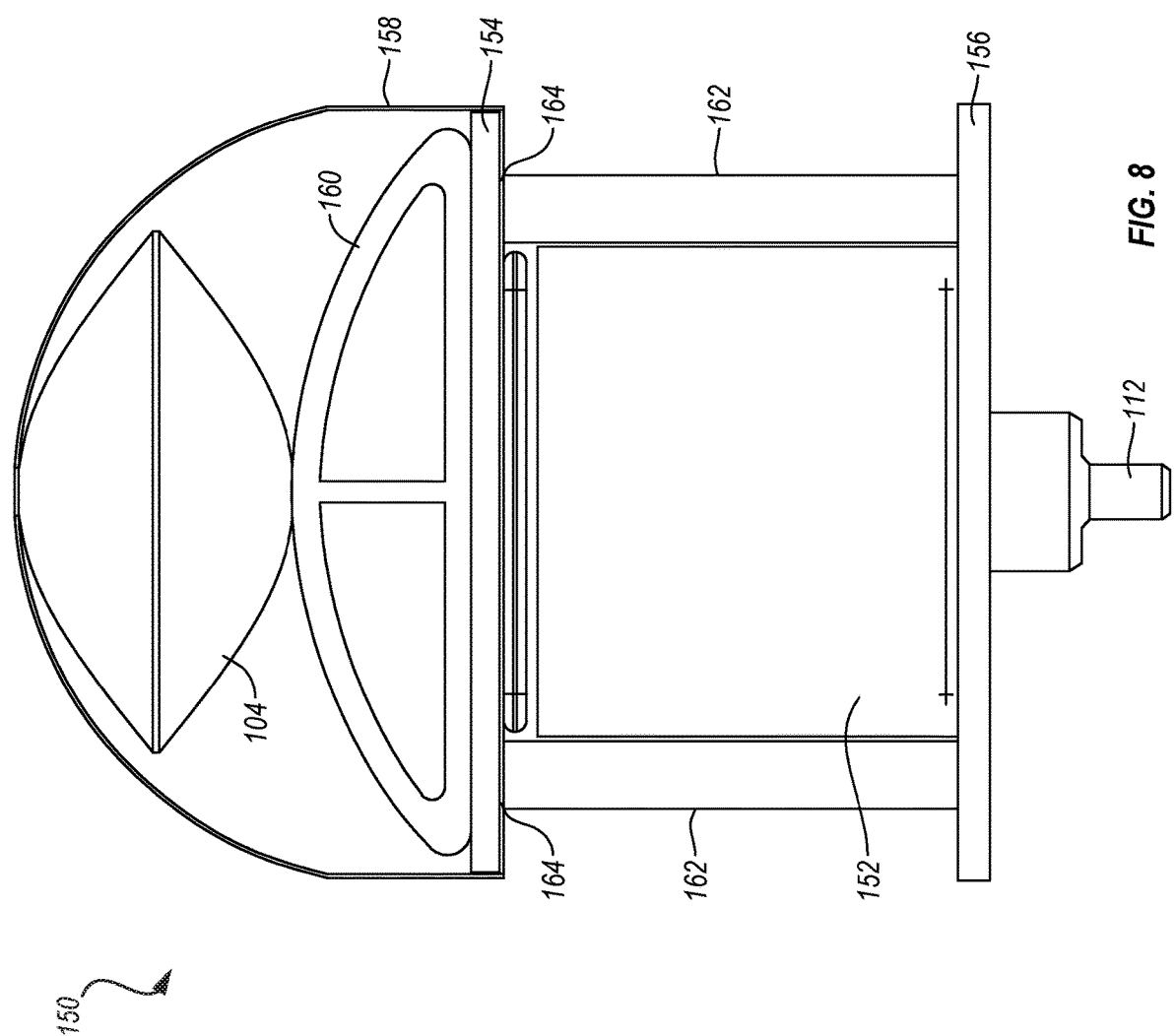
FIG. 8 depicts a top view of the vacuum-assisted irrigation pump shown in FIG. 7.
Figure 9:
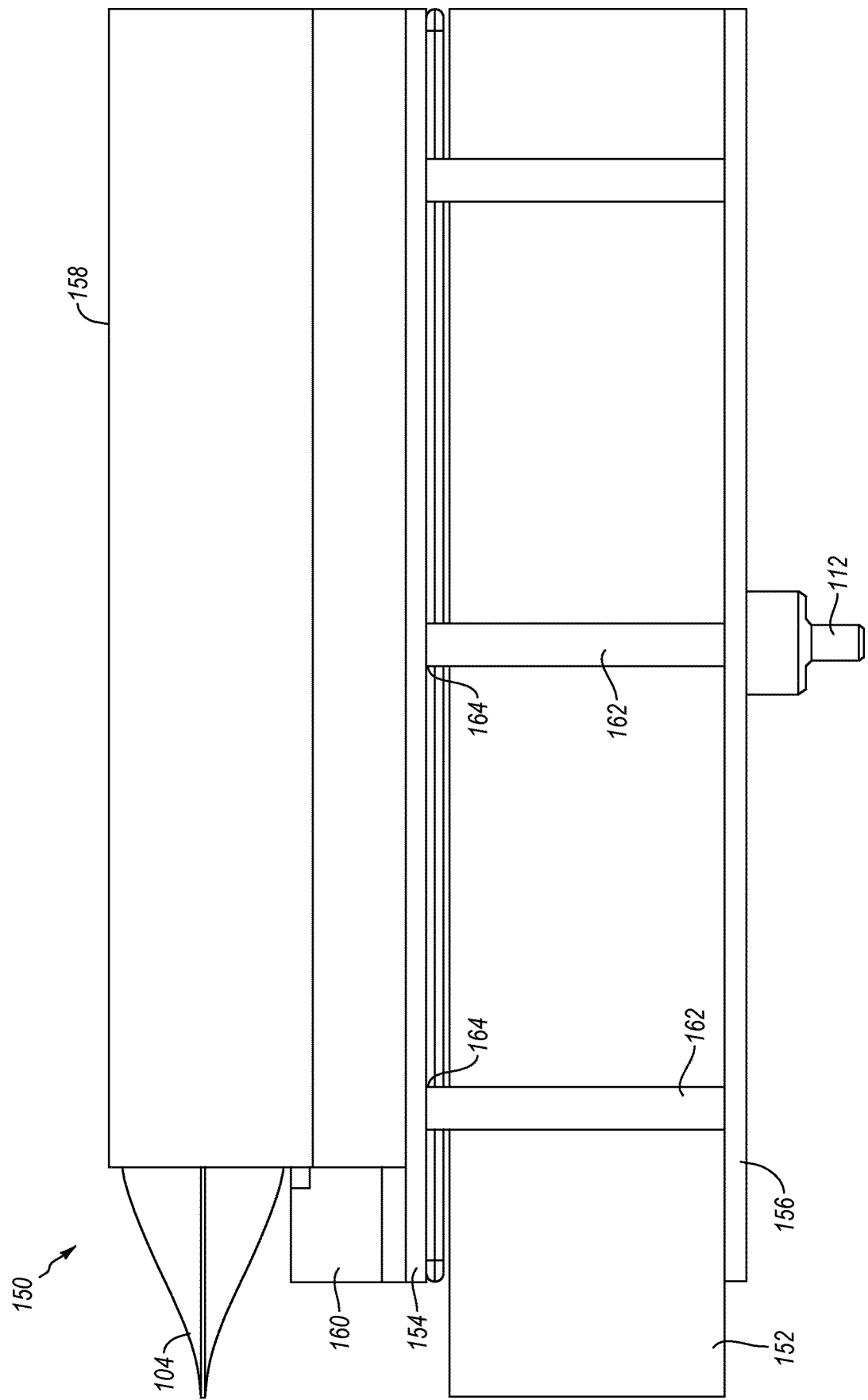
FIG. 9 depicts a side view of the vacuum-assisted irrigation pump shown in FIG. 7.

FIG. 6D depicts an alternative embodiment in which the compressive members 108 are curved and exhibit some amount of compliance under the force of the pressure differential to allow some elastic deformation of the compressive members 108. In such an embodiment, the compressive members 108 may have a progressive compliance or a uniform compliance with a progressive curvature that allows for a progressive compression of the fluid reservoir 104. In providing compressive members 108 with either a progressive compliance or progressive curvature, a compression from one side of the fluid reservoir 104a to a second side of the fluid reservoir 104b, and therefore, a more complete emptying of the fluid reservoir may be attained. The embodiments described herein may be utilized independently or in combination to achieve different performance in a variety of applications.

In an alternative embodiment depicted in FIGS. 7-10, an irrigation pump 150 may use at least one compressible chamber 152 to pressurize a fluid reservoir 104 that is external to the compressible chamber 152. The compressible chamber 152 may be at least partially evacuated to create a negative pressure therein using a substantially similar method as described earlier in conjunction with the flexible envelope 102 of irrigation pump 12. In an embodiment, the compressible chamber 152 may have or be connected to a top plate 154 and a bottom plate 156 on opposing sides of the compressible chamber 152, such that when a negative pressure is created within the compressible chamber 152, a net pressure differential due to atmospheric pressure will urge the top plate 154 and the bottom plate 156 toward one another. In another embodiment, the top plate 154 and bottom plate 156 may be integral with and form surfaces of the compressible chamber 152.

An upper compressive member 158 may be affixed to the top plate 154. In an embodiment, the upper compressive member 158 may be flexible, rigid, or semi-rigid. If the compressive member 158 is rigid or semi-rigid, the compressive member may be formed with a complementary shape to that of a lower compressive member 160 such that a surface of the lower compressive member 160 and a surface of the upper compressive member 158 may meet with substantially no space therebetween such that when a fluid reservoir 104 is disposed in that space, the fluid reservoir 104 will be compressed as completely as possible. Similarly, if the upper compressive member 158 is flexible, it may conform to the shape of the lower compressive member 160 such that there is substantially no space therebetween such that when a fluid reservoir 104 is disposed in that space, the fluid reservoir 104 will be compressed as completely as possible.

The lower compressive member 160 may be connected to the bottom plate 156 by a mechanical link. In an embodiment, the mechanical link may be a plurality of standoffs 162. The plurality of standoffs 162 may pass through a corresponding plurality of openings 164 in the top plate 154. Therefore, the irrigation pump 150 may comprise a compressive assembly comprising the upper compressive member 158 and top plate 154 and a rigid assembly comprising the lower compressive member 160, the bottom plate 156 and the plurality of standoffs 162. The compressible chamber 152 may connect the compressive assembly and the rigid assembly. The compressive assembly and rigid assembly may be substantially limited to one axis of motion relative to one another due to the plurality of standoffs 162 passing through the corresponding plurality of openings 164.

Figure 10:
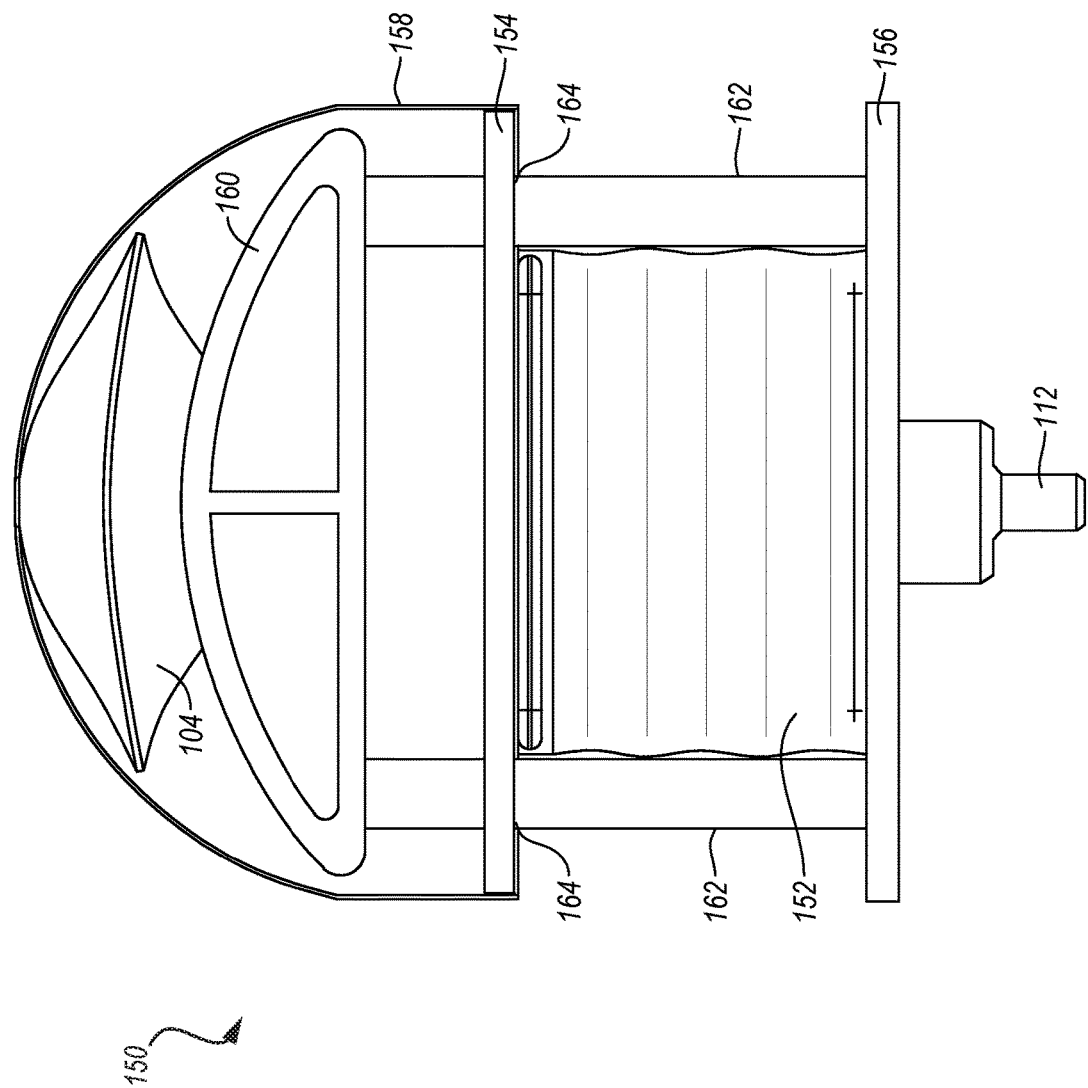
FIG. 10 depicts another top view of the vacuum-assisted irrigation pump of FIG. 7 showing the pump in use.

As shown in FIG. 10, when the compressible chamber 152 decreases in volume, the compressible chamber 152 moves the top plate 154 and the bottom plate 156 closer together. The top plate 154, being fixed to the upper compressive member 158, moves the upper compressive member 158 toward the bottom plate 156 as the top plate 154 moves toward the bottom plate 156. The bottom plate 156 and the lower compressive member 160 are held in fixed relation to one another by standoffs 162. As a result, when top plate 154 and upper compressive member 158 move closer to bottom plate 156, the lower compressive member 160 and the upper compressive member 158 may move toward each other and apply a force to the fluid reservoir 104 disposed therebetween.

Irrigation pump 150 may, therefore, transmit the force of the pressure differential between the interior and exterior of the compressible chamber 152 to the fluid reservoir 104 or other object disposed between the lower compressive member 160 and the upper compressive member 158. In addition, irrigation pump 150 may be easily reused by releasing the pressure on the compressible chamber 152 and simply exchanging an empty fluid reservoir 104 for a new, full fluid reservoir 104. Irrigation pump 150 may operate with minimal moving parts, yielding a reliable, low cost, and easily portable reusable device for the pressurization of fluid for medical procedures.

Figure 11:
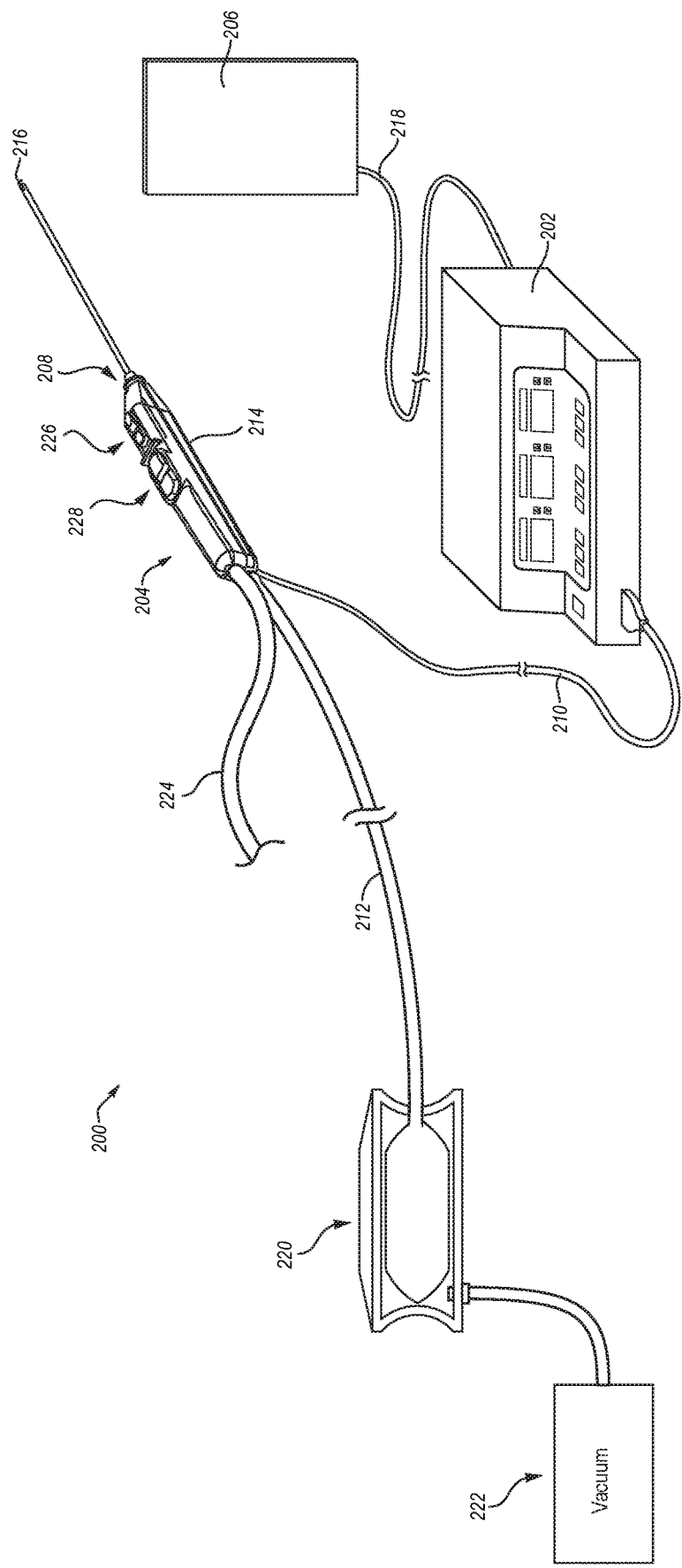
FIG. 11 depicts an electrosurgical system with irrigation capabilities according to one example embodiment of the present disclosure.

Attention is now directed to FIG. 11, which illustrates an electrosurgical system 200 that includes the irrigation functionality described herein. The illustrated embodiment includes a signal generator 202, an instrument 204, and a return electrode 206 for performing electrosurgical procedures. Generator 202, in one embodiment, is an RF wave generator that produces RF electrical energy. Generator 202 and instrument 204 are connected by a cable 210 that communicates electrical energy from generator 202 to instrument 204.

Generally, instrument 204 includes a hand piece or pencil 214 and an electrode tip 216. Instrument 204 communicates electrical energy to a target tissue of a patient to cut the tissue and/or cauterize blood vessels within and/or near the target tissue. Specifically, an electrical discharge is delivered from electrode tip 216 to the patient in order to cause heating of cellular matter of the patient that is in close contact with electrode tip 216. The tissue heating takes place at an appropriately high temperature to allow instrument 204 to be used to perform electrosurgery. Return electrode 206 is connected to generator 202 by a cable 218 in order to complete the circuit and provide a return electrical path to wave generator 202 for electrical energy that passes into the patient's body.

As shown in FIG. 11, instrument 204 is also connected to an irrigation tube 212 that conveys a sterile irrigation solution to instrument 204. Similar to the embodiments discussed above, an irrigation pump 220, which may be similar or identical to any of the other irrigation pumps discussed herein, may deliver the sterile irrigation solution to instrument 204 via irrigation tube 212 with energy provided by a vacuum 222. As with the other irrigation pumps discussed herein, irrigation pump 220 may use the force created by a pressure differential between the exterior atmospheric pressure and a partial vacuum disposed within the irrigation pump 220 to pump or otherwise drive the irrigation solution through irrigation tube 212 to instrument 204.

As also discussed above, the pressure differential may be provided by fluid communication of the irrigation pump 220 with the vacuum 222. The net force on the irrigation pump 220 may be used to pressurize a fluid reservoir and deliver a pressurized stream of fluid to the instrument 204. The pressurized stream of fluid may be discharged from instrument 204 through an opening or port 208 in hand piece 214. In some embodiments, electrode tip 216 is inserted into instrument 204 through opening 208 and includes a conduit therethrough. In such embodiments, the fluid may be discharged through from the conduit in electrode tip 216, rather than directly from the opening 208 in instrument 204.

According to the illustrated embodiment, instrument 204 can also be connected to a vacuum tube 224 to facilitate evacuation of smoke and/or fluid from a surgical site. Vacuum tube 224 can be connected to vacuum 222 or another vacuum source to draw the smoke and/or fluids into instrument 204 (e.g., through opening 208 and/or through the conduit in electrode tip 216) and through vacuum tube 224. Thus, instrument 204 can provide electrosurgical, irrigation, and smoke/fluid evacuation capabilities.

As can be seen in FIG. 11, instrument 204 includes a set of inputs 226 that control the electrosurgical functions (e.g., cut, coagulation, etc.) of instrument 204. For instance, inputs 226 can control the flow and type of electrical energy from generator 202 and the electrical discharge at electrode 216. Instrument 204 also includes a set of inputs 228 that control the irrigation/evacuation functions of instrument 204. For instance, one of inputs 228 may control the flow of irrigation fluid through instrument 204 while another of the inputs 228 may control the evacuation of smoke and/or fluid through instrument 204.

In light of the above, the irrigation pumps of the present disclosure allow for a portable source of pressurized irrigation fluid while utilizing the readily available central vacuum system in most modern hospitals or other vacuum pump.

Terms used herein, such as top, bottom, upper, and lower, are used simply for convenience in referring to certain elements of the disclosed embodiments and are not intended to limit the orientation or relative positioning of the disclosed embodiments or the individual elements thereof. Thus, for example, a top plate may be positioned below or to the side of a bottom plate, while a bottom plate may be positioned above or to the side of a top plate. Additionally, the terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for the pressurization of fluid for medical procedures, the device comprising:
a flexible envelope defining a flexible chamber, the flexible envelope being configured to house a fluid reservoir within the flexible chamber;
first and second compressive members in contact with and disposed on opposing sides of the flexible envelope, the first compressive member being selectively movable closer to the second compressive member to apply a compressive force to the fluid reservoir in response to a negative pressure within the flexible envelope;
a conduit configured to provide fluid communication between an exterior of the flexible envelope and the flexible chamber.

2. The device of claim 1, further comprising a retention device disposed on a surface of the flexible envelope and configured to retain at least one of the first or second compressive members.

3. The device of claim 2, wherein the retention device comprises at least one sleeve connected to the flexible envelope, the at least one sleeve being configured to receive the at least one of the first or second compressive members at least partially therein.

4. The device of claim 1, wherein the second compressive member is selectively movable closer to the first compressive member to apply a compressive force to the fluid reservoir.

5. The device of claim 1, wherein the first and second compressive members are movably connected to one another.

6. The device of claim 1, wherein at least one of the first or second compressive members is integrated into a surface of the flexible envelope.

7. A device for the pressurization of fluid for medical procedures, the device comprising:
a plurality of compressive members configured to apply a force to a fluid reservoir disposed between the plurality of compressive members;
a substantially air-tight flexible envelope configured to apply a force to the plurality of compressive members when a volume of the flexible envelope decreases; and
a valve in fluid communication with the flexible envelope, the valve being configured to allow for the creation of a negative pressure within the flexible envelope.

8. The device of claim 7, wherein the plurality of compressive members are disposed within the interior of the flexible envelope.

9. The device of claim 7, wherein the plurality of compressive members pivotally connected together.

10. The device of claim 7, wherein the plurality of compressive members have complementarily shaped surfaces.

11. The device of claim 7, wherein at least one compressive member of the plurality of compressive members is elastically deformable.

12. The device of claim 7, wherein at least one compressive member of the plurality of the compressive members has a curved surface.

13. The device of claim 7, wherein at least one compressive member of the plurality of compressive members is integrated into a surface of the flexible envelope.

14. The device of claim 13, wherein at least one compressive member of the plurality of compressive members forms a surface of the flexible envelope.

15. A device for the pressurization of fluid for medical procedures, the device comprising:
a flexible envelope defining an interior volume, the flexible envelope being configured to receive a fluid reservoir therein;
a reservoir connection configured to convey fluid from the fluid reservoir within the flexible envelope to a location outside of the flexible envelope;
first and second compressive members associated with the flexible envelope and configured to be disposed on opposing sides of the fluid reservoir disposed within the flexible envelope; and
a vacuum connection associated with the flexible envelope, the vacuum connection being configured to enable the evacuation of the flexible envelope,
wherein evacuation of the flexible envelope is configured to cause the first and second compressive members to move closer together and apply a force to the fluid reservoir disposed within the flexible envelope, wherein the force applied to the fluid reservoir is configured to cause a fluid within the fluid reservoir to exit the fluid reservoir through the reservoir connection.

16. The device of claim 15, wherein the first and second compressive members are disposed inside of the flexible envelope.

17. The device of claim 16, wherein the first and second compressive members are secured in place by one or more sleeves, adhesives, or hook-and-loop fasteners.

18. The device of claim 15, wherein the first and second compressive members are hingedly connected to one another.

19. The device of claim 15, wherein the flexible envelope further comprises an opening to facilitate the insertion or removal of the fluid reservoir into or from the flexible envelope.

20. The device of claim 19, wherein the opening is configured to be closed in an air-tight manner.

* * * * *